(12) United States Patent
Guan et al.

(10) Patent No.: US 7,785,357 B2
(45) Date of Patent: Aug. 31, 2010

(54) EXPANDING PLUG FOR TENDON FIXATION

(75) Inventors: Zhixu Guan, Bonita Springs, FL (US); Gerlinde Michel, Munich (DE)

(73) Assignee: Arthrex, Inc., Naples, FL (US)

( * ) Notice: Subject to any disclaimer, the term of this patent is extended or adjusted under 35 U.S.C. 154(b) by 694 days.

(21) Appl. No.: 11/637,943

(22) Filed: Dec. 13, 2006

(65) Prior Publication Data
US 2007/0156151 A1 Jul. 5, 2007

Related U.S. Application Data

(60) Provisional application No. 60/750,066, filed on Dec. 14, 2005.

(51) Int. Cl.
*A61B 17/84* (2006.01)
(52) U.S. Cl. ...................... 606/326; 606/328
(58) Field of Classification Search .................. 606/63, 606/75, 139, 144–145, 148–149, 151, 232, 606/233, 323, 326, 327–328; 623/13.14, 623/13.17, 23.48, 23.5, 13.15–13.16
See application file for complete search history.

(56) References Cited

U.S. PATENT DOCUMENTS

| | | | | | |
|---|---|---|---|---|---|
| 5,059,193 | A | * | 10/1991 | Kuslich | 606/247 |
| 5,236,431 | A | * | 8/1993 | Gogolewski et al. | 606/139 |
| 5,472,452 | A | * | 12/1995 | Trott | 606/232 |
| 5,741,282 | A | * | 4/1998 | Anspach et al. | 606/151 |
| 5,906,632 | A | * | 5/1999 | Bolton | 606/232 |
| 6,203,572 | B1 | * | 3/2001 | Johnson et al. | 623/13.15 |
| 6,328,758 | B1 | * | 12/2001 | Tornier et al. | 606/232 |
| 6,533,816 | B2 | * | 3/2003 | Sklar | 623/13.14 |
| 2002/0068939 | A1 | * | 6/2002 | Levy et al. | 606/63 |
| 2003/0187444 | A1 | * | 10/2003 | Overaker et al. | 606/72 |
| 2007/0032793 | A1 | * | 2/2007 | Del Rio et al. | 606/72 |

FOREIGN PATENT DOCUMENTS

WO    WO 2005048856 A1 *  6/2005

* cited by examiner

*Primary Examiner*—Thomas C Barrett
*Assistant Examiner*—Larry E Waggle, Jr.
(74) *Attorney, Agent, or Firm*—Dickstein Shapiro LLP

(57) ABSTRACT

An expanding plug for tendon fixation features a two-part system in which an expansion pin fits inside a fixation sleeve. The fixation sleeve is configured to expand diametrically to achieve interference fixation of a graft tendon inside of a bone tunnel. Fixation sleeve expansion is urged by a two-step engagement of the expansion pin. The tendon graft is assembled to the expanding bolt and situated within a bone tunnel. Passing suture is used to pull a joint-line end of the expansion pin into the tunnel to partially expand the fixation sleeve at the joint-line end. Pulling a graft end of the expansion pin toward the joint line expands the fixation sleeve to place the expanding plug in the fully deployed configuration.

6 Claims, 6 Drawing Sheets

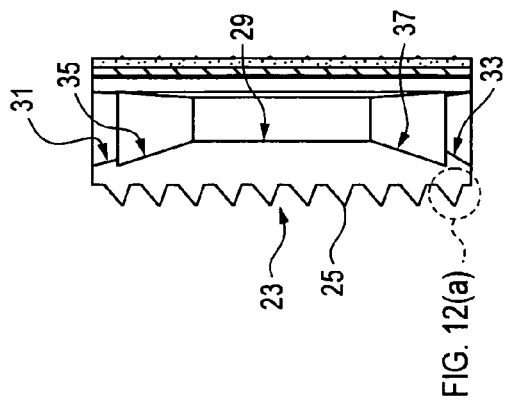
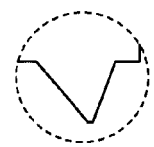
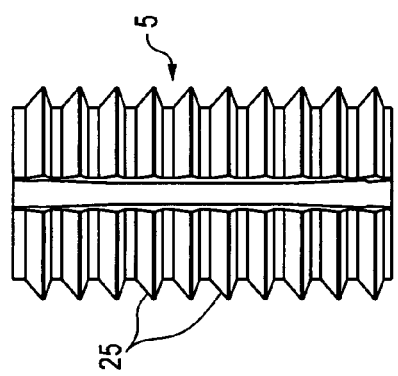
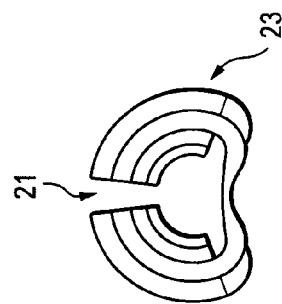
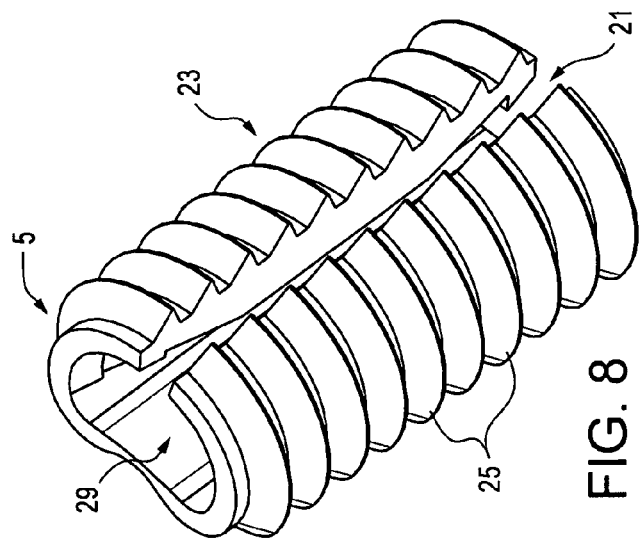
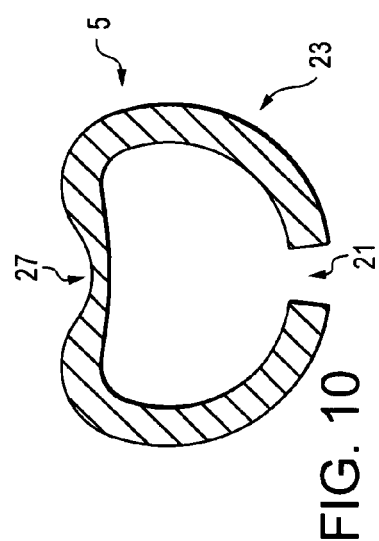

EXPANDING PLUG FOR TENDON FIXATION

CROSS-REFERENCE TO RELATED APPLICATIONS

This application claims the benefit of U.S. Provisional Application Ser. No. 60/750,066, filed Dec. 14, 2005, the entire disclosure of which is incorporated by reference herein.

BACKGROUND OF THE INVENTION

1. Field of the Invention

The present invention relates to apparatus and methods for surgically anchoring replacement tendon constructs.

2. Description of the Related Art

When soft tissue such as a ligament or a tendon becomes detached from a bone, surgery is usually required to reattach or reconstruct the tissue. Often, a tissue graft is attached to the bone to facilitate regrowth and permanent attachment. Various fixation devices, including sutures, screws, staples, wedges, and plugs have been used in the past to secure soft tissue to bone. In typical interference screw fixation, for example, the graft is fixed to the bone by driving the screw into a blind hole or a tunnel in the bone while trapping the end of the graft between the screw and the bone tunnel. In other methods, the graft is simply pinned against the bone using staples or sutures tied around the end of the graft to the bone.

More recently, various types of threaded suture anchors have been developed. The application of such suture anchors generally requires the surgeon to tie knots in the suture to secure the tissue to the bone, which is tedious and time-consuming. The surgical procedure would be less cumbersome for the surgeon and ultimately more beneficial to the patient if the tissue could be attached to the bone without the surgeon having to tie suture knots.

Accordingly, a need exists for secure and simplified methods and devices for anchoring tendon grafts.

SUMMARY OF THE INVENTION

The present invention overcomes disadvantages of the prior art, such as those noted above, by providing an expanding plug for soft tissue fixation (for example, for tendon fixation). The expanding plug features a two-part system in which an expansion pin fits inside a fixation sleeve. The fixation sleeve is configured to expand diametrically to achieve interference fixation of soft tissue (for example, graft tendon) in a bone tunnel.

Fixation sleeve expansion is urged by at least one-step engagement of the expansion pin, preferably a two-step engagement of the expansion pin. The graft is assembled to the expanding bolt and situated within a bone tunnel. Passing suture is used to pull a first end (joint-line end) of the expansion pin into the tunnel to partially expand the fixation sleeve at the first end (joint-line end). This first step of the expanding pin deployment allows for self-retaining of the expansion pin while further deployment is performed. Further deployment may be accomplished by pulling a second end (graft end) of the expansion pin toward the first end (joint-line end). This optional second step further expands the fixation sleeve with the expanding bolt in the fully deployed configuration.

Other features and advantages of the present invention will become apparent from the following description of the invention, which refers to the accompanying drawings.

BRIEF DESCRIPTION OF THE DRAWINGS

FIGS. 7(*a*)-(*f*) are various cross-sectional views of the expansion pin of FIG. 7;

FIG. 8 is a perspective of a fixation sleeve according to the present invention;

FIG. 9 is a front elevation of the fixation sleeve shown in FIG. 8;

FIG. 10 is a graft-end view of the fixation sleeve FIGS. 8 and 9;

FIG. 11 is a joint-line end view of the fixation sleeve shown in FIGS. 8-10;

FIG. 12 is a side elevation of the fixation sleeve shown in FIGS. 8-11;

FIG. 12(*a*) is an enlarged view of detail A of FIG. 12;

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The expanded plug of the present invention is a two-part system comprising an expansion pin that fits inside a fixation sleeve. The fixation sleeve is configured to expand diametrically to achieve interference fixation of a graft tendon in a bone tunnel. Preferably, the fixation sleeve expansion is urged by a two-step engagement of the expansion pin. The graft (for example, tendon graft) is assembled to the expanding bolt and then situated within a bone tunnel. A passing strand (for example, suture) is used to pull a joint-line end of the expansion pin into the tunnel to partially expand the fixation sleeve at the joint-line end. This first step of the expanding pin deployment allows for self-retaining of the expansion pin while further deployment is performed.

As explained in more detail below, further deployment may be accomplished by pulling a graft end of the expansion pin toward the joint line. This optional second step further expands the fixation sleeve with the expanding bolt in the fully deployed configuration.

Figure 1:
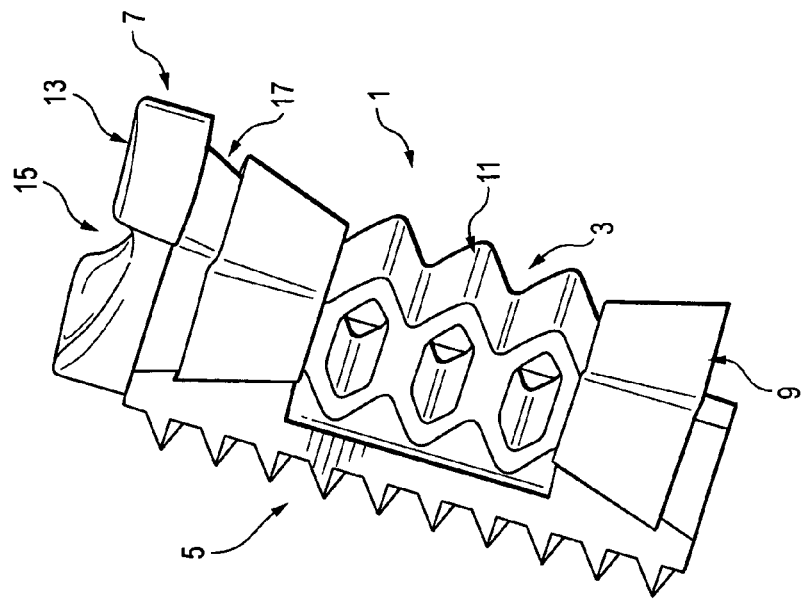
FIG. 1 is a partially-cutaway graphical perspective of an undeployed tendon fixation plug according to the present invention.
Figure 2:
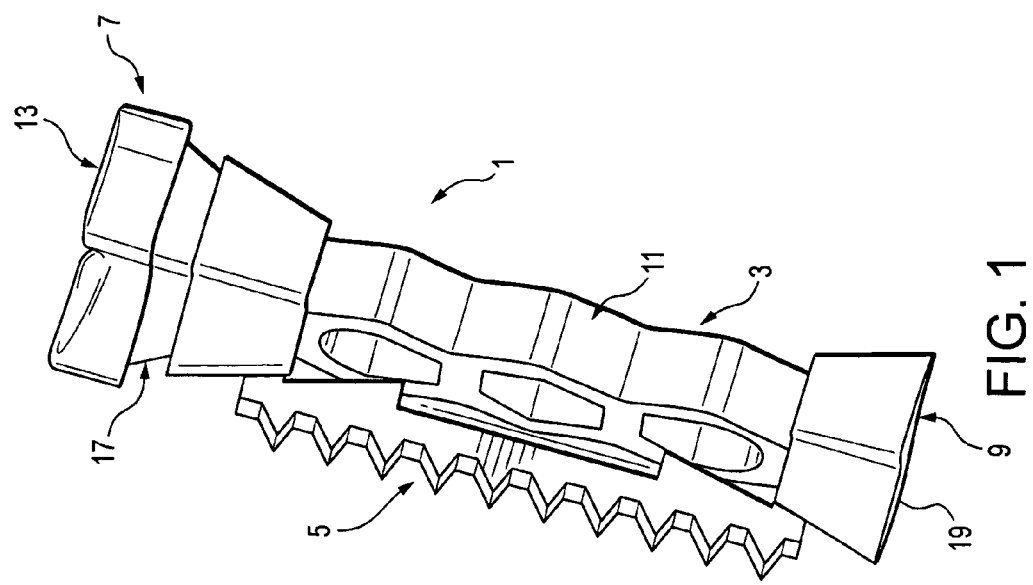
FIG. 2 is a partially-cutaway graphical perspective of a fully-deployed tendon fixation plug according to the present invention.
Figure 5:
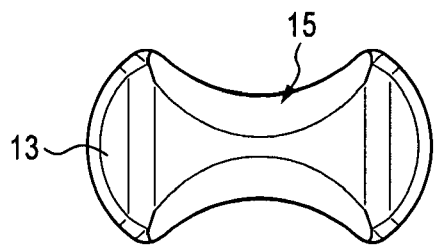
FIG. 5 is a graft-end view of the expansion pin shown in FIGS. 3 and 4.

Referring now to the drawings, where like elements are designated by like reference numerals, an exemplary expanding plug 1 of the present invention is illustrated in FIGS. 1 and 2. Expanding plug 1 is undeployed prior to installation as shown in FIG. 1. Upon installation, expanding plug 1 is deployed as shown in FIG. 2. Installation and deployment of expanding plug 1 are described further and in more detail below.

As shown in FIGS. 1 and 2, expanding plug 1 includes an expansion pin 3 and a fixation sleeve 5. Expansion pin 3 is illustrated in more detail in FIGS. 3-7. Fixation sleeve 5 is illustrated in more detail in FIGS. 8-12.

Figure 3:
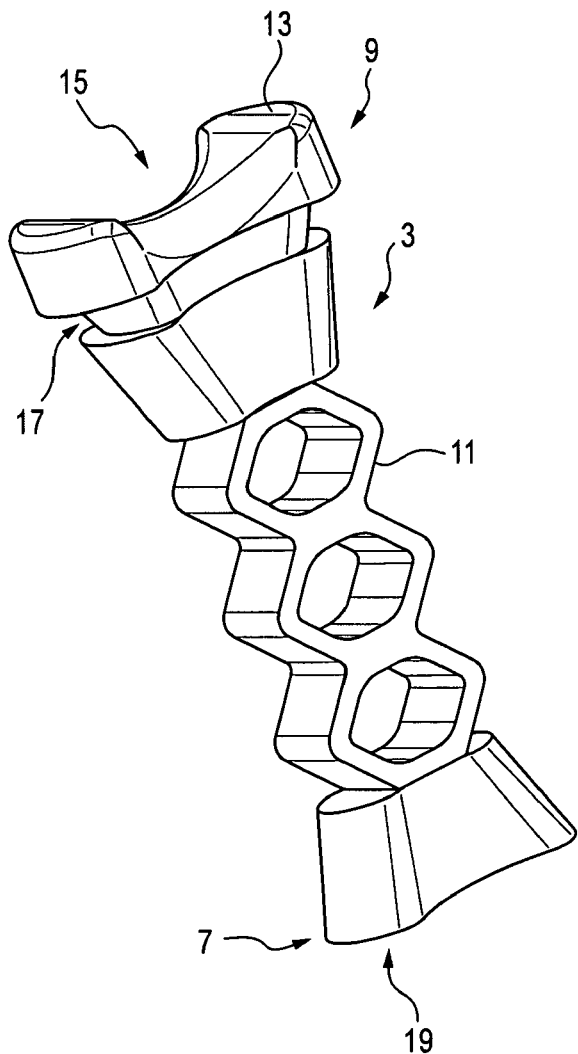
FIG. 3 is a perspective of an expansion pin according to the present invention.

Referring initially to FIG. 3, expansion pin 3 features a graft end 7, an opposing joint-line end 9, and a spring 11 extending between the two ends 7, 9. Graft end 7 has an oblong cross-section, as shown best in FIG. 5, and a generally wedge-shaped profile shown in FIG. 4. Spring 11 is attached at the narrowest portion of the wedge-shaped graft end 7. Graft end 7 tapers outward as it extends from the spring 7 attachment to terminate at a bridge portion 13. Bridge portion 13 features a U-shaped graft-cradling cleft 15. A notch 17 formed circumferentially into graft end 7 is provided for locking engagement with a corresponding feature on the inside of fixation sleeve 5 as described further below.

Figure 4:
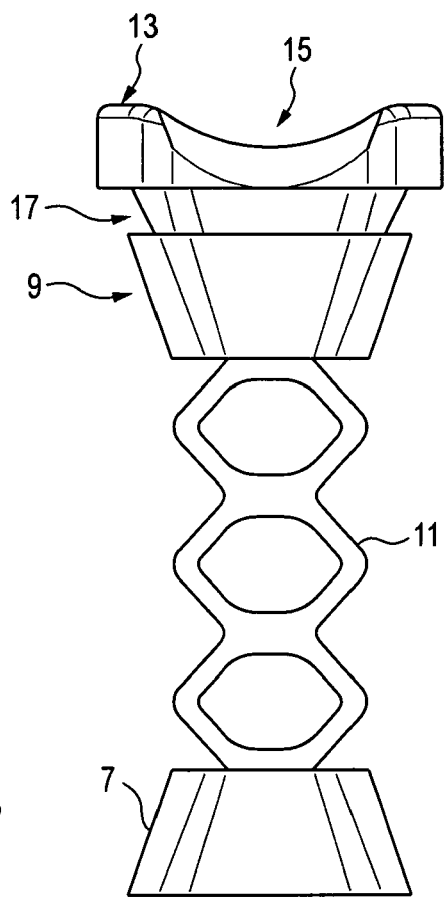
FIG. 4 is a front elevation of the expansion pin shown in FIG. 3.
Figure 6:
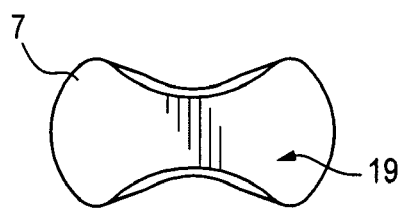
FIG. 6 is a joint-line end view of the expansion pin shown in FIGS. 3-5.
Figure 7:
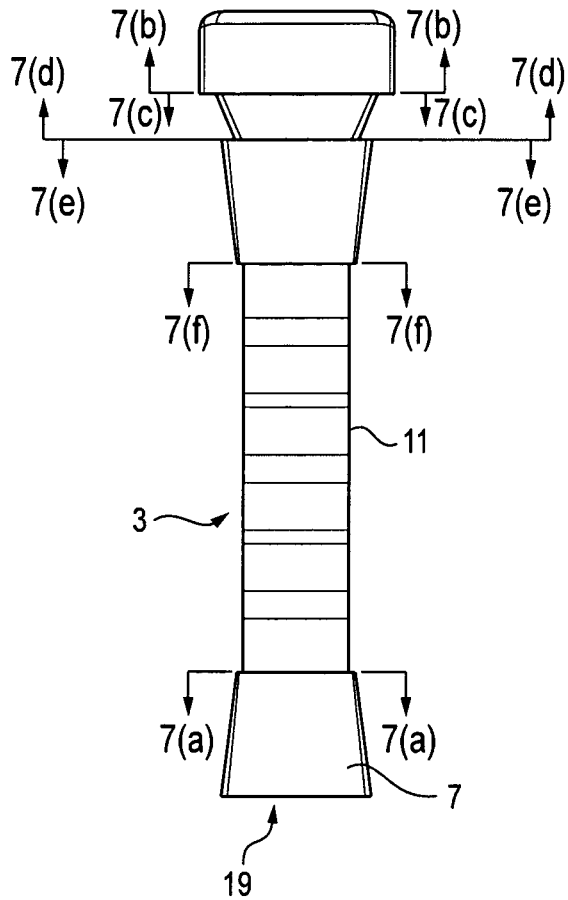
FIG. 7 is a side elevation of the expansion pin shown in FIGS. 3-6.
Figure 7A:
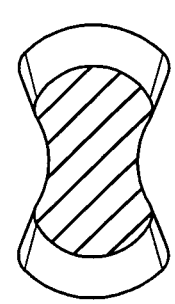
Figure 7B:
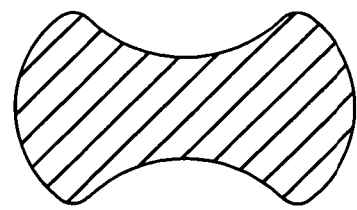
Figure 7C:
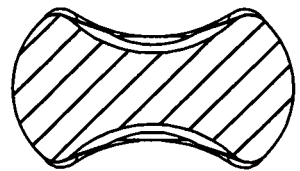
Figure 7D:
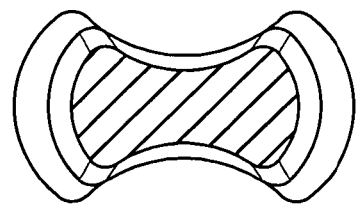
Figure 7E:
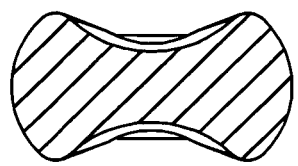
Figure 7F:
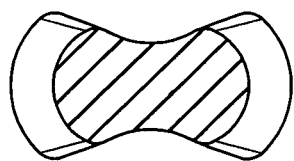

Joint-line end 9 of expansion pin 3 also has an oblong cross-section, shown in FIG. 6, and a generally wedge-shaped profile, similar to but varied from those of graft end 7. Joint-line end 9 has no graft-cradling cleft. In addition, joint-line end 9, as shown in FIGS. 3, 4, and 7, for example, has no circumferentially-formed notch. Instead, locking engagement of the joint-line end 9 inside fixation sleeve 5 is against a proximal face 19 of joint-line end 9.

The expansion pin 3 fits fixation sleeve 5 of expanding plug 1. Referring to FIG. 8-11, fixation sleeve 5 has a cannulated kidney-shaped cross-section and a generally rectangular profile. Fixation sleeve 5 features an axial split 21 along one side to allow fixation sleeve 5 to spread diametrically in response to the urging of expansion pin 3, as described below. An outer surface 23 of fixation sleeve 5 features protuberances 25 illustrated as circumferential barbs 25. Barbs 25 engage bone tunnel inner surfaces and tendon graft outer surfaces to enhance interference fixation of the graft inside the bone tunnel.

Reference is now made to FIGS. 10 and 11. A thin wall 27 is featured on the side of the fixation sleeve 5 opposite axial split 21. Thin wall 27 provides flexible relief to ease spreading of the fixation sleeve and to evenly distribute expansion forces. Thin wall 27 features geometry and curvature designed such that the stress is evenly distributed along the structure. Thin wall 27 also allows large deformation without breaking.

As shown in FIG. 12, an inner surface 29 of fixation sleeve 5 is provided with locking devices (for example, hooks) 31, 33. Hooks 31, 33 engage respective corresponding features on expansion pin 3 (notch 17, proximal face 19) for locking engagement upon deployment of expansion pin 3 within fixation sleeve 5.

Inner surface 29 is also provided with sloped faces 35, 37. Sloped faces 35, 37 cooperate respectively with the wedge-shaped sides of graft-end 7 and joint-line end 9 of expansion pin 3 to spread fixation sleeve 5 open. The cooperative engagement of the sloped faces 35, 37 and wedge-shaped sides also prevents the expansion pin 3 from sliding axially out of fixation sleeve 5. The respective slopes of these cooperating surfaces are such that expansion of fixation sleeve 5 is favored over squeezing the expansion pin 3 and urging it axially so as to avoid having expansion pin 7 "spring back" out of fixation sleeve 5.

Figure 13:
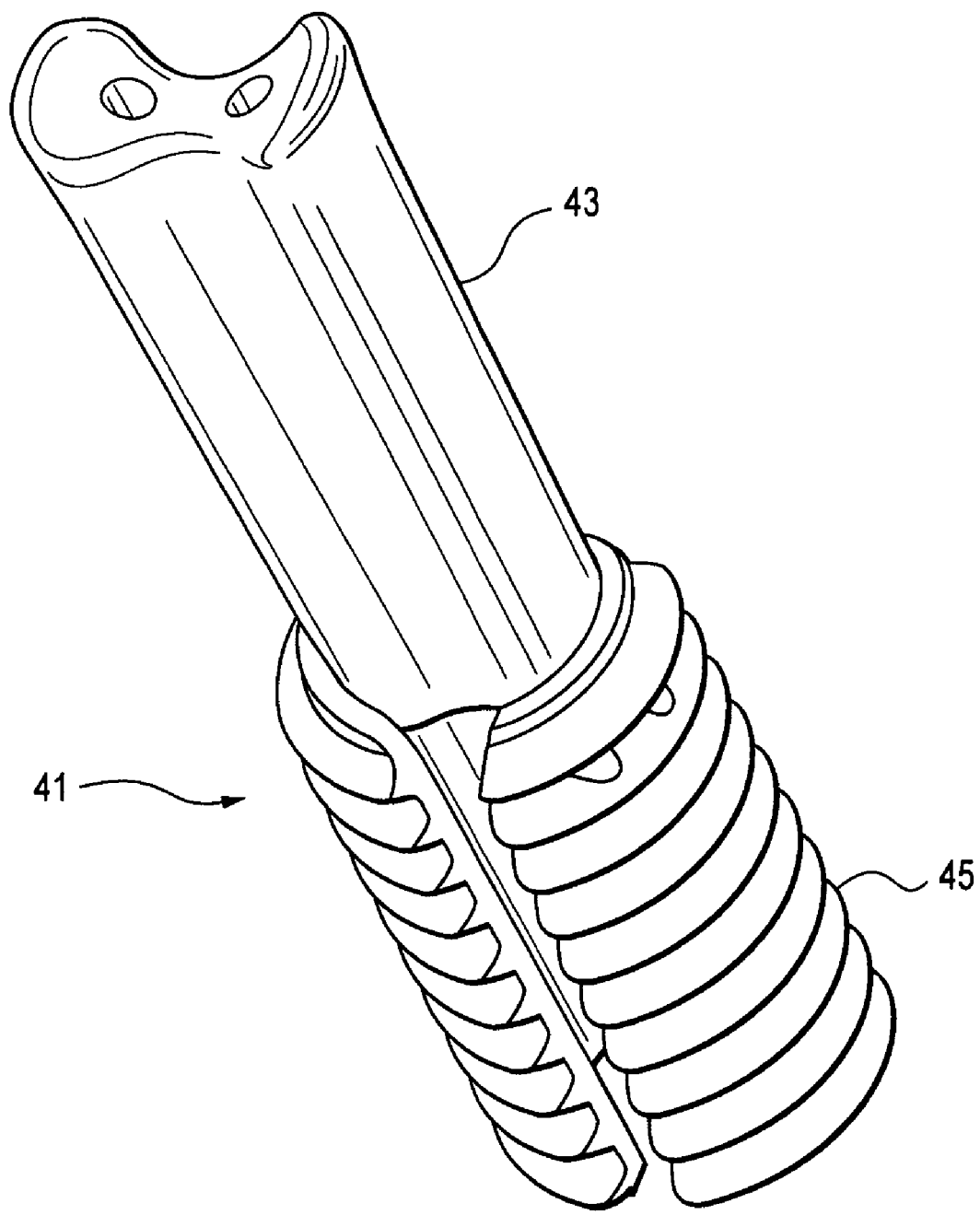
FIG. 13 is a perspective of an expanding plug tendon fixation device according to an alternative embodiment of the present invention.

FIG. 13 illustrates an alternative embodiment of the present invention as exemplified by a simplified expanding plug 41. Expanding plug 41 features a tapered expansion pin 43 and a basic fixation sleeve 45. Outer surface features similar to barbs 25 on expanding plug 1 enhance graft fixation. Additional fixation can be provided using suture. The expansion pin 43 is urged axially to spread open and expand basic fixation sleeve 45.

Expanding plugs or anchors according to the present invention can be used for arthroscopic procedures such as ligament repairs. The plugs are also advantageous for open and mini-open surgical procedures. Specific examples of applicable procedures include cortical bone-soft tissue fixation, Bankart and SLAP shoulder repairs.

Figure 14:
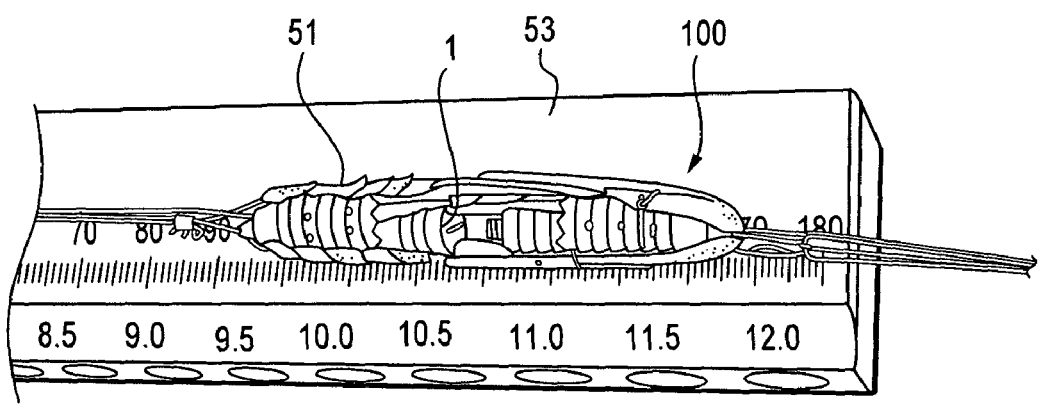
FIG. 14 illustrates a graft tendon assembled to an expansion plug tendon fixation device according to the present invention.

A surgical method employing an expanding plug, such as the expanding plug 1 of FIGS. 1-12, generally includes preforming a hole or tunnel (for example, a femoral tunnel) for insertion of the plug. The expanding plug 1 (attached to a graft) is then inserted into the hole/tunnel and then expanded. FIG. 14 illustrates an exemplary graft/plug assembly 100 comprising graft tendon construct 51 tied to expanding plug 1 according to a method of the present invention. In the exemplary embodiment of FIG. 14, the graft construct 51 is formed as a continuous loop sutured together around expanding plug 1 on a graft workstation 53. The expanding plug 1 spaces the tendon strands apart to create a double-bundle configuration. Suture is used to maintain placement of the tendon graft strands around the plug and to create a desired length graft.

The graft/plug assembly 100 is installed into a tunnel (for example, femoral tunnel) by guiding the assembly oriented with graft-end 7 entering the tunnel and pulling the assembly up into the tunnel using a passing strand (for example, suture) engaging the joint-line end. Further pulling on the joint-line end passing suture begins initial deployment of expanding plug 1. Thus, joint-line end 9 of expansion pin 3 is urged by the load being applied by pulling on the passing suture to partially-expand fixation sleeve 5 at the end nearest the knee by the cooperation with sloped surface 37.

The applied load causes spring 11 to deflect. With sufficient deflection of spring 11, proximal surface 19 of joint-line end 9 engages hook 33 and locks into place. The graft end 7 is drawn against the graft 51 during this process. The partially-expanded fixation sleeve 5 provides sufficient fixation to ensure that the expanding plug 1 is self-retaining within the femoral tunnel during subsequent steps described following.

According to a preferred embodiment, the expanding plug 1 may be additionally, fully deployed by way of an optional (second) step in which graft end 7 is pulled toward the joint line end using another set of passing strands (for example, suture strands). The load is applied in an opposite direction to that described above for the initial first step of deployment. Spring 11 is further deflected under the load so as to engage notch 17 and hook 31. The expanding plug 1 thereby achieves the deployed configuration shown in FIG. 2.

The arrangement of plug 1 that allows for the exemplary two-step deployment procedure provides certain advantages over simplified plug 41 shown in FIG. 13. These advantages include: (i) an ability to shorten the overall length of the plug from 30 mm or longer to about 20 mm; (ii) preassembly of the two pieces for ease of insertion; (iii) mutually-increased ease of each of the first and second deployment steps as compared to expanding the sleeve using a single expansion pin, resulting in lower deployment force; and (iv) overall deployment force preferably is less than about 20 lbs to about 30 lbs.

Although expansion pin 3 has been shown and described as a single piece, the expansion pin can be alternatively provided as a two-part system, for example, as well as other configurations. In addition, the two parts could be connected by suture or a frangible plastic section. It is also possible to provide additional parts or features that provide mechanical assistance in opening and spreading the fixation sleeve to press against the femoral tunnel walls.

Any expanding plastic polymer can be used for the expanding plug 1. Preferably, the material can be drilled out of bone with a drill and would be acceptable to the FDA as an implant grade material. The diameter of the implants and looped graft together preferably does not exceed about 10 mm, on average, with a double-wrapped autograft semitendinosis graft or a single tibialis tendon allograft. The diameter of the implant should be approximately 5 mm expanding to a minimum of 10 mm at body temperature. Maximum resistance of graft pullout in porcine bone sockets equal to the diameter of the graft preferably is not less than 500 N.

Advantageously, the expanding plug 1 of the present invention is a self-reinforcing structure. The greater the load applied on the graft-end 7 toward the knee, the more expanding and compression into the bone tunnel walls is achieved, resulting in higher pullout strength.

At least one hole may be preferably provided through the expanding plug 1 to allow a secure suturing to the graft and bone growth infiltration. Preferably, the device is sutured to the graft with multiple holes to fixate graft free ends. Multiple holes also reduce the amount of PLLA and allow accelerated tissue/bone in growth. Fixation within the tunnel may be further enhanced or provided with backup fixation using additional suture.

The present invention provides a low profile construction with the graft looped around the bottom and slots on the side to accommodate the graft strands. It is not necessary to enlarge the overall bone tunnel size needed. A FiberWire tensioner could provide quantifiable tensioning during device expansion with no. 5 FiberWire.

The two parts of the expansion plug 1 can be molded together with a thin plastic bridge connection between the two components. The thin plastic connection may be configured to break during deployment. This will keep the parts aligned during suturing to the graft and insertion.

Using the present invention, the expansion process can be completed within one minute in human body temperatures. The implant can retain mechanical strength for three months in human cyclic clone modeling. Additional strands (for example, one to two no. 5 FiberWire sutures) may be attached to the base of the expandable plug for graft passing and backup fixation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method of arthroscopic surgery, the method comprising the acts of:
    attaching a tissue graft to an expanding assembly comprising an expansion pin and a fixation sleeve configured to engage the expansion pin and to expand diametrically to achieve interference fixation of the graft inside of a bone opening, the tissue graft being attached to the expanding assembly by placing the tissue graft around the expanding assembly and securing the tissue graft around the expanding assembly;
    situating the expanding assembly with the attached tissue graft within at least a portion of a bone opening;
    positioning a first end of the expanding assembly into the bone opening to partially expand the expanding assembly at the first end, so as to self-retain the expanding assembly within the bone opening;
    pulling a second end of the expanding assembly toward the first end to further expand the fixation sleeve; and
    expanding the assembly into a fully deployed configuration.

2. The method of claim 1, wherein the bone opening is a bone tunnel.

3. A method of tendon repair using a tendon graft, the method comprising the acts of:
    providing an expanding bolt comprising an expansion pin and a surrounding expansion sleeve configured to engage the pin and to expand diametrically to achieve interference fixation of the graft inside of a bone opening;
    placing a tendon graft around the expanding bolt and suturing the tendon graft to the expanding bolt to attach the tendon graft to the expanding bolt;
    providing the tendon graft attached to the expanding bolt within a bone tunnel;
    pulling a first end of the expansion pin into the tunnel in a first direction, to partially expand the fixation sleeve; and
    pulling a second end of the expansion pin in a second direction which is opposite the first direction, to fully expand the fixation sleeve and to achieve interference fixation of the tendon graft inside the bone opening.

4. The method of claim 3, wherein pulling the first end of the expansion pin into the tunnel to partially expand the fixation sleeve comprises the step of engaging the expansion pin with a first notch of the fixation sleeve.

5. The method of claim 3, wherein pulling the second end of the expansion pin to fully expand the fixation sleeve comprises the step of engaging the expansion pin with a second notch of the fixation sleeve.

6. The method of claim 3, wherein the step of fully expanding the fixation device comprising reducing the length of the pin from about 30 mm to about 20 mm.

* * * * *